US009795585B2

(12) United States Patent
Liu et al.

(10) Patent No.: US 9,795,585 B2
(45) Date of Patent: Oct. 24, 2017

(54) METHODS OF USING L-BUTYLPHTHALIDE FOR THE PREVENTION AND TREATMENT OF CEREBRAL ISCHEMIA DISEASE

(75) Inventors: Zhentao Liu, Hebei Province (CN); Hongwu Zhang, Hebei Province (CN); Zhanqi Niu, Hebei Province (CN); Dongmin Shen, Hebei Province (CN); Rongduan Wang, Hebei Province (CN); Xiaolong Feng, Hebei Province (CN)

(73) Assignee: CSPC Zhongqi Pharmaceutical Technology (Shijizhuang) Co. Ltd., Hebei (CN)

( * ) Notice: Subject to any disclaimer, the term of this patent is extended or adjusted under 35 U.S.C. 154(b) by 0 days.

(21) Appl. No.: 11/458,650

(22) Filed: Jul. 19, 2006

(65) Prior Publication Data

US 2007/0167516 A1    Jul. 19, 2007

Related U.S. Application Data

(63) Continuation of application No. PCT/CN2005/000064, filed on Jan. 17, 2005.

(30) Foreign Application Priority Data

Jan. 20, 2004 (CN) .......................... 2004 1 0001748

(51) Int. Cl.
  *A61K 31/33* (2006.01)
  *A61K 31/343* (2006.01)
(52) U.S. Cl.
  CPC .................................. *A61K 31/343* (2013.01)
(58) Field of Classification Search
  None
  See application file for complete search history.

(56) References Cited

U.S. PATENT DOCUMENTS

2007/0112065 A1   5/2007  Feng et al.
2011/0082201 A1   4/2011  Feng et al.

FOREIGN PATENT DOCUMENTS

| CN | 1100097 A | 3/1995 |
| CN | 1257706 A | 6/2000 |
| CN | 1605336 A | 4/2005 |
| EP | 1679070 A1 | 7/2006 |
| EP | 1757286 A1 | 2/2007 |

OTHER PUBLICATIONS

Iadecola (Cerebral Ischemia: Molecular and Cellular Pathophysiology, Wolfgang Walz, ed.,1999).*
Guo et al Meta-analysis of defibrase in treatment of acute cerebral infarction (Chin Med J 119(6):662-668, 2006).*
Shimamura et al. Novel Therapeutic Strategy to Treat Brain Ischemia: Overexpression ofEdema in Rat Model Hepatocyte Growth Factor Gene Reduced Ischemic Injury Without Cerebral (Circ 109:424-431,2004).*
Yan et al (Acta Pharmacoligica Sin 29:117-120, 1998).*
Yan et al (Yao Xue Xue Bao 33:418-423, 1998) Abstract Only.*
Yamori et al (Stroke 8:456-461, 1977).*
Williams et al (Foye's Principles of Medicinal Chemistry, 5th Edition, p. 50, 2002).*
del Zoppo (Curr Op Hematol 7:309-315, 2000).*
Xu et al (Yao Xue Xue Bao 36:329-333, 2001; Abstract only).*
De Geyter et al (J Neuroinflammation 9:114-126, 2012).*
GOOGLE translation of Feng et al (CN 1086942 C (2000)).*
Hesselink (Imaging of Stroke and Cerebral Ischemia, available online at http://spinwarp.ucsd.edu; accessed Feb. 18, 2015).*
Yang et al (Stroke 23(9):1331-1336, 1992).*
"International Search Report for Application No. PCT/CN2005/000064", 2 Pages.
Dun, H. U., et al., "Effect of dl-n-butylphthalide on memory disturbance induced by focal cerebral ischemia in rats", *Chinese Journal of Pharmacology and Toxicology*, vol. 11(1), (Feb. 1997).
Yan, C.-H., et al., "Effect of dl-n-butylphthalide on striatum cerebral blood flow in normal and middle cerebral artery occlusion in rats", *Chinese Journal of Pharmacology and Toxicology*, vol. 12(1), (Feb. 1998).
"European Application Serial No. 05700438.4, Communication and European Search Report dated Jan. 12, 2010", 8 pgs.
Chang, Q., et al., "Effects of chiral 3-n-butylphthalide on apoptosis induced by transient focal cerebral ischemia in rats", *Acta Pharmacologica Sinica*, 24(8), (Aug. 2003), 796-804.
Chong, Z., et al., "dl-3-n-butylphthalide reduces brain damage in mice with closed head injury", *Chinese Medical Journal*, 113(7), (2000), 613-616.
Chong, Z. Z., et al., "Effect of dl-3-n-butylphthalide on the activity of the choline acetyltransferase in ischemic brain and cultured neurons subjected to hypoglycemia/hypoxia", *Zhongguo Yaoxue Zazhi—Chinese Pharmaceutical Journal*, 34(8), (w/ English Abstract), (1999), 519-522, Abstract Only.
Feng, Y. P., et al., "Effect of DL-butylphthalide (NBP) on mouse brain energy metabolisum in complete brain ischemia induced by decapitation", *Yao Xue Xue Bao / Acta Pharmaceutica Sinica*, 30(10), (Abstract Only), (1995), 1 pg, Abstract Only.
Lin, J. F., et al., "Effect of DL-3-N-butylphthalide on delayed neuronal damage after focal cerebral ishemia and intrasynaptosomes calcium in rats", *Yaoxue Xuebao*, 31(3), (Abstract Only), (1996), 2 pgs, Abstract Only.
Liu, X, G., et al., "Protective effect of dl-3-n-butylphthalide on ischemic neurological damage and abnormal behavoir in rats subject to focal ischemia", *Yao Xue Xue Bao / Acta Pharmaceutica Sinica*, 30(12), (Abstract Only), (Dec. 1995), 2 pgs.

(Continued)

*Primary Examiner* — Craig Ricci
(74) *Attorney, Agent, or Firm* — Schwegman Lundberg & Woessner, P.A.

(57) ABSTRACT

The inventive subject matter relates to the use of L-butylphthalide in the manufacturing of medicaments for the prevention and treatment of cerebral ischemia-induced disease. Cerebral ischemia of the animals or human induces cerebral infarction, neurological deficit, memory disorder, cerebral edema, cerebral apoplexy, metabolic disorder of energy, changes of cerebral blood flow, and the like. The in vivo experiments show that L-butylphthalide can effectively reduce the above-mentioned adverse symptoms induced by cerebral ischemia.

6 Claims, No Drawings

(56) References Cited

OTHER PUBLICATIONS

Peng, Y., et al., "Effects of chiral NBP on cerebral infarct volume due to transient focal cerebral ischemic", *Chinese Journal of New Drugs*, 14(4), (w/ English Abstract), (2005), 420-423, Abstract Only.

Xiong, J., et al., "The protective effect of butylphthalide against mitochondrial injury during cerebral ischemia", *Yaoxue Xuebao*, 35(6), (Abstract Only), (Jun. 2000), 2 pgs, Abstract Only.

Xu, H., et al., "Effects of 3-n-Butylphalide on Pial Arterioles in Focal Cerebral Ischemia Rats", *Acta Pharmaceutica Sinica*, 34(3), (w/ English Abstract), (Mar. 1999), 172-175, Abstract Only.

Xu, H.-L., et al., "Inhibitory Effects of chiral 3-n-butylphthalide on inflammation following focal ischemic brain injury in rats", *Acta Pharmacologica Sinica*, 21(5), (Abstract Only), (May, 2000), 2 pgs, Abstract Only.

Yu, S.-R., et al., "Facilitated performance of learning and memory in rats by 3-n-butyl phthalide", *Acta Pharmacologica Sinica*, 9(5), (w/ English Abstract), (Sep. 1988), 385-388, Abstract Only.

Zhang, L. Y., et al., "Effect of dl-3-n-butylphthalide (NBP) on life span and neurological deficit in SHRsp rats", *Yao Xue Xue Bao / Acta Pharmaceutical Sinica*, 31(1), (Abstract Only), (1996), 2 pgs, Abstract Only.

"European Application Serial No. 05700438.4, Office Action mailed Oct. 7, 2011", 7 pgs.

"European Application Serial No. 05700438.4, Response filed Feb. 7, 2012 to Office Action mailed Oct. 7, 2011", 8 pgs.

"European Application Serial No. 05700438.4, Summons to Attend Oral Proceedings mailed Jul. 19, 2013", 6 pgs.

"International Application Serial No. PCT/CN2005/000064, Written Opinion mailed May 26, 2005", (w/ English Translation), 8 pgs.

Deng, W., et al., "Effect of dl-3-n-butylphthalide on brain edema in rats subjected to focal cerebral ischemia", (Abstract), [online]. Database Accession No. NLM11324493, Database Medline. US National Library of Medicine (NLM), (Jun. 1997), 2 pgs.

Wang, X.-W., "3-n-Butylphthalide—cerebral antiischemic", *Drugs of the Future*, 25(1), (2000), 16-23.

"Japanese Application Serial No. 2006-549834, Office Action dated Mar. 30, 2010", (w/ English Translation), 7 pgs.

"Japanese Application Serial No. 2006-549834, Office Action dated Feb. 22, 2011", (w/ English Translation), 4 pgs.

Deng, W., et al., "Effect of dl-3-n-butylphthalide on brain edema in rats subjected to focal cerebral ischemia", *Chin Med. Sci. J.*, 12(2), 102-206, (Abstract Only), (1997), 1 pg.

Murakami, H., "18—Utilization of Optically Active Substances", *Chemistry Foundation Quarterly*, No. 6, Published by Yoshida Shinki, Tokyo, Japan (w/ English Translation), (1999), 7 pgs.

Yokoyama, T., "Optical Isomer Determining Drug's Efficacy", *Journal of Clinical and Experimental Medice*, 160, p. 382, (w/ English Translation), 3 pgs.

Martz, Dean, et al., "Dimethylthiourea Reduces Ischemic Brain Edema Without Affecting Cerebral Blood Flow", *Journal of Cerebral Blood Flow and Metabolism*, 10(3), (1990), 352-357.

Mellergård, Pekka, et al., "Time Course of Early Brain Edema Following Reversible Forebrain Ischemia in Rats", *Stroke*, 20(11), (Nov. 1989), 1565-1570.

Raslan, Ahmed, et al., "Medical management of cerebral edema", *Neurosurg Focus*, 22(5), (2007), 1-12.

Sapolsky, Robert M., "Glucocorticoids Potentiate Ischemic Injury to Neurons: Therapeutic Implications", *Science*, 229, (1985), 1397-1400.

Siegel, Barry A., et al., "Steroid Therapy of Brain Edema—Ineffectiveness in Experimental Cerebral Microembolism", *Arch Neurol*, 27, (Sep. 1972), 209-212.

Zhang, et al., "", 16-19.

"Disorders of Energy Metabolim", [online]. [retrieved on Oct. 16, 2013]. Retrieved from the Internet: <URL: http://accessmedicine.com/content.aspx?aid-6588606>, (2013), 1 pg.

"Disorders of Energy Metabolism, Family Practice Notebook", [online]. © 2013 Family Practice Notebook, LLC. [retrieved on Oct. 16, 2013]. Retrieved from the Internet: <URL: http://www.fpnotebook.com/Endo/Metabolism/DsrdrsOfEnrgy/Mtblsm.htm>, (2013), 5 pgs.

"European Application Serial No. 05700438.4, Response filed Oct. 22, 2013 to Summons maiiled Jul. 19, 2013", 11 pgs.

"Japanese Appeal No. 2014-5386, Appeal Decision mailed Aug, 4, 2015", (w/ English Translation), 19 pgs.

"The Center for Inherited Disorders of Energy Metabolism, Case Western Reserve University", [online]. [archived on Sep. 12, 2013]. Retrieved from the Internet: <URL: https://web.archive.org/web/20130912175345/http://www.cwru.edu/med/CIDEM/cidem.htm>, (2013), 1 pg.

Miyazaki, Hiroshi, et al., "Bioactivity of Optically Active Substances", Separation of Enantiomers (Quarterly Chemical Review No. 6), Jun. 10, 1999 (third book), 16-29 (English Translation of Relevant Parts, p. 16, Lines 8 to 15), (1999), 1 pg.

Murakami, Naomichi, "Use of Optically Active Substances", Quarterly Chemical Review No. 6, Jun. 10, 1999 (third book), 212-225 (English Translation of Relevant Parts, p. 212, lines 12 to 24), (1999), 1 pg.

Yamanaka, Hiroshi, et al., "Preparation of Optically Active Substance", Separation of Enantiomers (Quarterly Chemical Review No. 6), Jun. 10, 1999 (third book), 2-14 (English Translation of Relevant Parts, p. 2, Lines 3 to 12), (1999), 1 pg.

Bardutzky, Juergen, et al., "Antiedema Therapy in Ischemic Stroke", http://stroke.ahajournals.org/content/38/11/3084, (Sep. 27, 2007), 3084-3094.

* cited by examiner

METHODS OF USING L-BUTYLPHTHALIDE FOR THE PREVENTION AND TREATMENT OF CEREBRAL ISCHEMIA DISEASE

RELATED APPLICATIONS

This application is a continuation under 35 U.S.C. §111(a) of International Application No. PCT/CN2005/000064, filed Jan. 17, 2005 and published as WO 2005/072725 A1 on Aug. 11, 2005, which claimed priority under 35 U.S.C. §119 to China Application No. 200410001748.X, filed Jan. 20, 2004, which applications and publication are incorporated herein by reference and made a part hereof.

FIELD OF THE INVENTION

The inventive subject matter relates to a new use of L-butylphthalide in the prevention and treatment of cerebral ischemia-induced diseases, particularly to a use of L-butylphthalide in manufacturing the medicaments for the prevention and treatment of cerebral ischemia-induced diseases.

BACKGROUND OF THE INVENTION

Butylphthalide can be illustrated by the following structure:

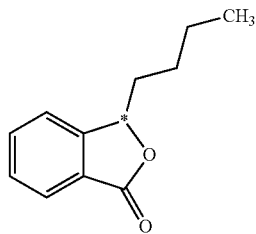 [SMILES: CCCC*1oc(=O)c2ccccc12]

There are two optical isomers of butylphthalide, the levo-butylphthalide (l-NBP) and dextro-butylphthalide (d-NBP), due to the presence of one chiral carbon atom therein. L-butylphthalide can be obtained directly by extracting the natural celery seeds, but can also be prepared synthetically. Chinese Patent No. 99109673.8 and Junshan Yang, Yalun Su, Acta Pharmaceutica Sinica, 1984, 31:671 both disclose procedures to obtain L-butylphthalide.

Furthermore, Chinese Patent No. 98125618.X discloses the use of L-butylphthalide in manufacturing a medicament against thrombosis and platelet aggregation, and shows clearly that L-butylphthalide has the effect of regulating NOS-NO-cGMP systemic function and arachidonic acid metabolism in the neurocytes post cerebral ischemia. In addition, Chinese Patent No. 93117148.2 discloses the use of racemic butylphthalide in manufacturing a medicament for the prevention and treatment of cerebral ischemia-induced diseases in mammals or human beings.

Accordingly, what is needed is the discovery of further pharmacological effects of L-butylphthalide, for example, via animal assay, which would provide new methods of treatment and medical uses of L-butylphthalide.

SUMMARY OF THE INVENTION

The invention provides a new use of L-butylphthalide.
The inventive subject matter relates to the use of L-butylphthalide in manufacturing the medicaments for the treatment of cerebral ischemia-induced diseases in the mammals or human beings.

Particularly, the inventive subject matter relates to the use of L-butylphthalide in manufacturing the medicaments for the treatment of neurological symptoms caused by cerebral injury-induced cerebral ischemia.

Particularly, the inventive subject matter relates to the use of L-butylphthalide in manufacturing the medicaments for the treatment of memory disorder induced by cerebral ischemia.

Particularly, the inventive subject matter relates to the use of L-butylphthalide in manufacturing the medicaments for the treatment of cerebral edema induced by cerebral ischemia.

Particularly, the inventive subject matter relates to the use of L-butylphthalide in manufacturing the medicaments for the treatment of cerebral apoplexy induced by cerebral ischemia.

Particularly, the inventive subject matter relates to the use of L-butylphthalide in manufacturing the medicaments for the treatment of metabolic disorder of energy induced by cerebral ischemia.

Particularly, the inventive subject matter relates to the use of L-butylphthalide in manufacturing the medicaments for the treatment and prevention of changes of cerebral blood flow in the ischemic region of brain.

Particularly, the inventive subject matter relates to the use of L-butylphthalide in manufacturing the medicaments for the treatment of behavioral disorder and cerebral infarction induced by permanent cerebral ischemia.

Particularly, the inventive subject matter relates to the use of L-butylphthalide in manufacturing the medicament for the treatment of disorder of neurological function and cerebral infarction induced by ischemia-reperfusion.

In vivo animal experiments show that L-butylphthalide has the following functions:
1. significantly reducing the neural symptoms caused by cerebral injury-induced cerebral ischemia in rats;
2. reducing memory disorder induced by cerebral ischemia in rats;
3. reducing cerebral edema induced by cerebral ischemia in rats;
4. reducing cerebral apoplexy induced by cerebral ischemia in rats;
5. reducing the metabolic disorder of energy induced by cerebral ischemia in rats;
6. increasing cerebral blood flow in the ischemic region;
7. reducing behavioral disorder induced by ischemia in rats;
8. reducing the cerebral infarct area induced by cerebral ischemia in rats.

The inventor has completed the inventive subject matter on the basis of the above-mentioned in vivo animal experiments.

The advantage of the inventive subject matter lies in the therapeutic effect of L-butylphthalide on the diseases induced by cerebral ischemia.

DETAILED DESCRIPTION OF THE INVENTION

The invention will be described by the in vivo animal experimental data, in order to illustrate the invention to one of skill in the art.

EXAMPLES

The following Examples are illustrative of the above invention. One skilled in the art will readily recognize that the techniques and reagents described in the Examples suggest many other ways in which the inventive subject matter could be practiced. It should be understood that many variations and modifications may be made while remaining within the scope of the invention.

Example 1

Effects of L-butylphthalide on Neural Symptoms Induced by Cerebral Injury in Rats Experimental Animals: male Wistar rats Experimental Methods: Cerebral injury in rats was caused by allowing a cone-shaped metal object weighing 220 g to freely fall from a position of 30 cm height and to strike the skull cap behind the left coronal suture. dl-, d-, and l-NBP (50 mg/kg) and the vehicle (control group) were orally administered after 5 minutes, and the behavioral changes were scored after 24 hours.

Experimental Results: Cerebral ischemia-induced neural symptom occurred in rats due to the cerebral injury. After orally administration, neural symptoms in l-NBP group was significantly reduced as compared with the vehicle control, while no significant effect was observed in the case of dl- and d-NBP groups, showing that l-NBP has significant reducing effect on neural symptoms caused by cerebral injury-induced cerebral ischemia.

Example 2

Effects of L-butylphthalide on Memory Disorder Induced by Focal Cerebral Ischemia Experimental Animal: The same as Example 1.
Experimental Equipment: Shuttle box.
Experimental Methods:
1. Rats were trained to acquire learning and memory;
2. Artery ligation: Artery ligation was conducted on rats according to the method of Tamura. After 24 hours, the experiment of learning as in step (1) was repeatedly conducted on rats.
3. Grouping and administration: the rats were divided into 9 groups, which were normal group, pseudo-operation group, ischemia control group, and groups of dl-, d-, and l-NBP (15 and 30 mg/kg). The rats were orally administered at 15 min after the operation, and the changes of latency of active and passive avoidance response were observed after 24 hours.

Experimental Results: As compared with the normal group, the rats in the ischemia control group were observed to apparently lose the memory and have less active avoidance response, showing that the memory disorder occurred. As compared with the vehicle control group, the times of active avoidance of rats in l-NBP group was significantly increased, while such effect was not observed in the case of dl- and d-NBP at all doses, showing that l-NBP has the effect of reducing the memory disorder induced by focal cerebral ischemia.

Example 3

Effects of L-butylphthalide on Cerebral Edema Induced by Cerebral Artery Ligation in Rats Experimental Animals: the same as Example 1.
Experimental Equipments: Oxygen analyzer.
Experimental Methods: Cerebral edema was induced by the ligation of right middle cerebral artery of rats. After 15 minutes, dl-, d-, and l-NBP (40 and 80 mg/kg) were orally administered. The rats were sacrificed after 24 hours. The forebrain was removed, and the cerebral hemispheres on the left and right side were weighed. Dry weight was obtained by baking for 24 hours under 100° C. The weight of water in the brain tissue was thus calculated by subtracting of dry weight from wet weight. Then, the tissues was nitrified for 4 hours, and pH was adjusted by using HCl. Next, the ion selective electrode was connected onto the oxygen analyzer, and the concentrations of $Na^+$ and $K^+$ in the brain tissue were measured.

Experimental Results: l-NBP group was shown to significantly decrease the content of water and $Na^+$, and increase the content of $K^+$ in the brain in a dose-dependent manner, while d- and dl-NBP groups were shown to have no significant effect, suggesting the l-NBP can significantly reduce cerebral edema induced by focal cerebral ischemia. dl-NBP (80 mg/kg) was shown to decrease the content of water and Na+ and increase the content of K+ in the brain, but the effects had no statistical significance. This result was due to the presence of l-NBP (40 mg/kg) in dl-NBP (80 mg/kg), indicating that the presence of d-NBP in dl-NBP may antagonize the function of l-NBP.

Example 4

Effects of L-butylphthalide on Cerebral Apoplexy in Spontaneous Hypertension Rats Experimental Animals: spontaneous hypertensive rats of 6 weeks old.

Experimental Methods: Spontaneous hypertensive rats of 6 weeks old were divided into 8 groups with 10 rats per group. 0.8 to 0.9 g per day of common salt was administered starting from week 6. The amount of common salt was gradually increased up to 1.2 to 1.3 g per day. dl-, d-, and l-NBP (25 and 50 mg/kg/d), vehicle (control group) and Nimodipine (37 mg/kg/d) were orally administered respectively starting from week 8 till to 3 weeks after the occurrence of cerebral apoplexy. The scores of neurological deficit and the time of death were recorded.

Experimental Results: l-NBP was shown to significantly delay the time of the occurrence of cerebral apoplexy as compared with the vehicle control, indicating that it has the effect of preventing the occurrence of cerebral apoplexy. Furthermore, l-NBP was shown to significantly increase the viability after the occurrence of cerebral apoplexy and reduce neurological deficit in a dose-dependent manner, indicating that it has therapeutic effect on cerebral apoplexy induced by spontaneous hypertension. dl-NBP merely had such effect at relatively high doses, and the effect of which was similar with that of Nimodipine, indicating that the effect of l-NBP is higher than that of dl-NBP.

The effect of d-NBP was not significant, suggesting that l-NBP has preventive and therapeutic effect on cerebral apoplexy induced by severe hypertension in the patients.

Example 5

Effects of L-butylphthalide on Ischemic Cerebral Metabolism of Energy Induced by the Decapitation of Mice Experimental Animals: KunMing mice.
Test drug: injectable L-butylphthalide was formulated into an emulsion with Tween-80.
Experimental Methods: KunMing mice of 10 to 22 g were divided into 8 groups with 10 mice per group. dl-, d-, and l-NBP (50 and 100 mg/kg/d), sodium Phenobarbital (225 mg/kg ip.) and the vehicle were orally administered. Thirty minutes after administration, the mice were decapitated.

The time between the decapitation and homogenation, which was 15 seconds, was regarded as cerebral ischemic time. Centrifugation and isolation were conducted by the method of Folbergrova, and the contents of lactic acid, ATP and PCr were determined by enzymological method.

Experimental Results: In ischemic control group, the content of lactic acid in the brain was increased, and the contents of ATP and PCr were decreased. In positive control drug group (ip.), the content of lactic acid was significantly decreased, while the contents of ATP and PCr were increased. After oral administration of 50 and 100 mg/kg of l-NBP, the content of lactic acid was significantly decreased, while the contents of ATP and PCr were increased. The difference was very significant as compared with the control group. dl- and d-NBP groups had no such significant effect. The results show that l-NBP has the effect of improving the cerebral metabolism of energy.

Example 6

Effects of NBP on Focal Cerebral Blood Flow

Experimental Animals: Male wistar rats.
Experimental Equipments: SXP operating microscope, 62TZ-V model high frequency electrotome, solid positioner, Diamond Electro-Tech chemical microsensor 1231, two channel physiological parameter recorder.

Experimental Methods:
(1) dl-, d-, and l-NBP (15 and 30 mg/kg) and the vehicle were orally administered to the normal rats, and the changes of cerebral blood flow at different time after the administration were measured.
(2) ligation of cerebral artery was conducted on rats according to the method of Tamura. Oral administration was performed at 10 min after the operation. The rats were divided into 9 groups, which were normal group, pseudo-operation group, vehicle control group, and groups of dl-, d-, and l-NBP (15 and 30 mg/kg).

Experimental Results: The cerebral blood flow rate in the normal rats was significantly increased at 30 minutes after the administration of l-NBP. The cerebral blood flow rate was maintained at a relative high level till to 50 min after the administration, and the increasing extent was gradually decreased over the time, without any effect on the blood pressure. dl- and d-NBP had no such effects, indicating that l-NBP may increase cerebral blood flow and improve cerebral blood supply without substantially affecting the blood pressure.

After the ligation of artery, l-NBP (15 and 30 mg/kg) groups could significantly increase the focal blood flow in the corpus striatum, on the side of which the cerebral artery was blocked. The difference was significant as compared with the vehicle control group. In addition, there was also significant difference between the different amounts of drug, showing that the effect of l-NBP is dose-dependent. There was a similar increase in dl-NBP (30 mg/kg) group, but the effect had no statistical significance. No significant effect was observed in other test drug groups.

The result showing that l-NBP can not only increase the normal cerebral blood flow, but also increase the blood flow in the ischemic region.

Example 7

Effects of L-butylphthalide on Behavioral Disorder and Cerebral Infarct Area in Permanent Cerebral Ischemic Rats Experimental Animal: The same as Example 1.
Experimental Equipments: COOLPIX955 digital camera, 722 grating spectroscope, XHF-1 high-speed disperser, YKH-II liquid high-speed mixer, WZ-50C2 micro infusion pump.

Experimental Methods: Wistar rats were anesthetized by intraperitoneally injecting 12% chloral hydrate in 350 mg/kg, and fixed in lateral decubitus position. The skin at the midpoint on the line from exterior auditory canal to canthus was cut. The muscle was separated layer by layer to expose zygomatic arch and the squamous part of temporal bone. The zygomatic arch was scissored and then placed under an operating microscope.

A window of 2 mm diameter was drilled by using a dentistry drill at a position of 2 mm under the anterior joint between zygomatic arch and the squamous part of temporal bone, so as to expose the middle cerebral artery. A little piece of filter paper was applied onto the middle artery, and 10 µl of 50% $FeCl_3$ aqueous solution was dripped onto the filter paper. The filter paper was removed after 30 min, and washed with physiological brine. Two to three drops of penicillin ($1.6 \times 10^5$ U/mL) were added so as to prevent infection of the cut. Then the cut was sutured layer by layer.

Experimental Results:
1. Effects on the Neurological Function

The behavior of animals in pseudo-operation group was not significantly changed, and the scores in model control group were significantly different from those in pseudo-operation group (P<0.001). The improvement of the neurological deficit scores was observed after intravenously injection of l, dl and d-NBP in rats, as compared with model control group.

At 24 hours after the administration of dl-NBP at low, moderate and high doses, the scores were decreased by 15.6%, 21.9% and 37.5% respectively, with $ED_{30}$ of 7.2 mg/kg. In the case of l-NBP, the scores were decreased by 17.2%, 29.7% and 35.9% respectively, with $ED_{30}$ of 6.2 mg/kg. In the case of d-NBP, the scores were decreased by 17.2%, 21.9% and 28.1% respectively, with $ED_{30}$ of 12.4 mg/kg.

The effect of l-NBP was two times of that of d-NBP. The effect of the positive drug, Nimodipine, was significant.

2. Effects on Cerebral Infarct Area

The infarct area in the animals of model group was significantly increased as compared with that in the animals of pseudo-operation group. dl-NBP and d-NBP at the dose of 2.5 mg/kg was shown to have the tendency of reducing cerebral infarct area, but the effect was not significant. l-NBP was shown to significantly reduce cerebral infarct area in the cerebral ischemic rats. 5 and 10 mg/kg doses of l-NBP were show to significantly reduce cerebral infarct area of model rats, and the effect increased with the increasing of the dose.

As compared with the model control group, three doses of dl-NBP reduced cerebral infarct area by 29.2%, 35.2% and 44.4% respectively, with $ED_{40}$ of 7.1 mg/kg. Three doses of l-NBP reduced cerebral infarct area by 38.4%, 41.9% and 50.7% respectively, with $ED_{40}$ of 3.3 mg/kg. Three doses of d-NBP reduced cerebral infarct area by 27.2%, 32.7% and 39.9% respectively, with $ED_{40}$ of 10.3 mg/kg.

As calculated by converting into ED50, the effect of l-NBP was about 3.1 times of that of d-NBP. The effect of the positive drug, Nimodipine, was significant.

Example 8

Effects of L-butylphthalide on the Behavioral Disorder and Cerebral Infarct Area in the Cerebral Ischemia-Reperfusion Rats Experimental Animal: The same as Example 1
Experimental Equipments: The same as Example 7
Experimental Methods: The rats were anesthetized, and fixed in lateral decubitus position. Under the operating microscope, a midline neck skin incision was made to expose the left common cartotid artery. The surrounding nerves and fascia from the bifurcation of common carotid artery to the vascular of basis cranii were removed. Then, the branches of the external carotid artery, which were occipital artery, superior thyroid artery, lingual artery and maxillary artery, were sequentially separated, ligated and scissored.

The internal carotid artery was then separated and carefully separated free from vagus nerve. Pterygopalatine artery was ligated at the root of the internal carotid artery. A 6# needle for injection containing 3# nylon suture (diameter of 0.285 mm) was punctured into the free end of the external carotid artery, advancing the nylon suture into the blood vascular. The needle was carefully withdrawn, and the nylon suture was guided into the internal carotid artery from the distal end of the external carotid artery up till to Willis ring, so as to effectively block the middle cerebral artery.

Depending on the body weight, the distance from the inserted nylon suture to the bifurcation of common carotid artery was 18 to 20 mm. The free end of the external carotid artery and the nylon suture therein were ligated together, in order to prevent bleeding. The muscle and the skin were then sutured layer by layer, and penicillin was dropped to prevent infection. To effectively block the middle cerebral artery, the tip of the nylon suture was made round by burning with the flame, and coated with 0.1% of poly-L-lysine. The nylon suture was baked in a 60° C. oven for 1 hour.

Due to the ability of poly-L-lysine to binding the cell and the protein to the plastic surface, and thus allow the negative charged nylon suture changing into a positive charged one and attract the anion ionic part of the endothelial cell, the nylon suture was closely bond to the endothelial surface, so as to prevent the leakage of the blood from the surrounding of the suture. Only the internal carotid artery was separated from the animals of pseudo-operation group.

One hour after MCAO, the rats which did not show significant hemiplegia of upper limbs and which subsequently died were wed out. At 1.5 hours after the initiation of MCAO, the nylon suture within the lumen of the internal carotoid artery was carefully withdrawn, and the internal carotoid artery was allowed to reperfusion. The rats were then placed back into the cage.

Experimental Results:
1. Effects on the Neurological Function

The behavior of animals in pseudo-operation group was not significantly changed, while the scores in animals of model control group were significantly different from those in pseudo-operation group (P<0.001). The improvement of the neurological deficit scores was observed at 24 hours after intravenously injection of l, dl, and d-NBP. The potency of l, dl, and d-NBP had no significant difference. The effect of the positive drug, Nimodipine, was significant.

2. Effects on Cerebral Infarct Area

The infarct area in animals of model group was significantly increased as compared with that in pseudo-operating group. Intravenously administration of dl, l, and d-NBP were all shown to significantly reduce cerebral infarct area in the cerebral ischemia-reperfusion rats, and the effect increase with the increasing of the dose. As compared with the model control group, three doses of dl-NBP reduced cerebral infarct area by 37.9%, 48.5% and 59.2% respectively, with $ED_{50}$ of 5.5 mg/kg. Three doses of l-NBP reduced infarct area by 40.8%, 57.0% and 68.5% respectively, with $ED_{50}$ of 3.8 mg/kg. Three doses of dl-NBP reduced infarct area by 34.8%, 46.5% and 60.9% respectively, with $ED_{50}$ of 5.7 mg/kg.

As calculated by $ED_{50}$, the effect of l-NBP was about 1.5 times of that of d-NBP. The effect of the positive drug, Nimodipine, was significant.

All documents, patents, and other references listed above are hereby incorporated by reference for any purpose, as though individually incorporated by reference. The invention has been described with reference to various specific and preferred embodiments and techniques. However, it should be understood that many variations and modifications may be made while remaining within the spirit and scope of the invention.

What is claimed is:

1. A method of reducing the likelihood of developing ischemia-induced cerebral edema and/or reducing the severity of ischemia-induced cerebral edema, said method comprising orally administering to a patient an amount of L-butylphthalide that is about 2 mg/kg to about 100 mg/kg, wherein the L-butylphthalide is administered in a composition that is substantially free of D-butylphthalide and wherein said administration takes place within a period of about 30 minutes after the onset of cerebral ischemia.

2. The method of claim 1 wherein the amount of L-butylphthalide administered is about 5 mg/kg to about 50 mg/kg.

3. The method of claim 1 wherein the amount of L-butylphthalide administered is about 50 mg/kg to about 100 mg/kg.

4. The method of claim 1 wherein the amount of L-butylphthalide administered is about 2 mg/kg to about 4 mg/kg.

5. The method of claim 1 wherein the patient is a mammal.

6. The method of claim 1 wherein the patient is a human.

* * * * *

UNITED STATES PATENT AND TRADEMARK OFFICE
CERTIFICATE OF CORRECTION

PATENT NO. : 9,795,585 B2
APPLICATION NO. : 11/458650
DATED : October 24, 2017
INVENTOR(S) : Liu et al.

Page 1 of 1

It is certified that error appears in the above-identified patent and that said Letters Patent is hereby corrected as shown below:

On the Title Page

Item (30), in "Foreign Application Priority Data", in Column 1, Line 1, delete "2004 1 0001748" and insert --200410001748.X-- therefor Item (56), in Column 2, under "Other Publications", Line 2, delete "ofEdema" and insert --of Edema-- therefor Item (56), in Column 2, under "Other Publications", Line 5, delete "Pharmacoligica" and insert --Pharmacologica-- therefor Signed and Sealed this
Fourteenth Day of April, 2020

Andrei Iancu
*Director of the United States Patent and Trademark Office*